United States Patent [19]

Olenick et al.

[11] 4,346,608
[45] Aug. 31, 1982

[54] FLOAT DEVICE FOR DENSITY GRADIENT FRACTIONATION

[75] Inventors: John G. Olenick, Laurel; Patrick E. Lorenz, Olney, both of Md.

[73] Assignee: The United States of America as represented by the Secretary of the Army, Washington, D.C.

[21] Appl. No.: 174,069

[22] Filed: Jul. 31, 1980

[51] Int. Cl.³ .............................................. G01N 1/14
[52] U.S. Cl. .............................. 73/863.21; 73/864.24; 422/82; 422/101
[58] Field of Search ........... 73/864.01, 864.73, 864.34, 73/863.21, 864.11, 863.23; 422/72, 82, 101

[56] References Cited

U.S. PATENT DOCUMENTS

| | | | |
|---|---|---|---|
| 3,586,064 | 6/1971 | Brown | 73/864.24 |
| 3,590,889 | 7/1971 | Vannus | 73/864.01 X |
| 3,827,304 | 8/1974 | D'Autry | 73/864.21 |
| 3,957,654 | 5/1976 | Ayres | 422/72 X |
| 4,037,464 | 7/1977 | Wenander | 73/864.01 X |
| 4,197,735 | 4/1980 | Munzer et al. | 73/864.24 X |
| 4,203,840 | 5/1980 | Stoeppler et al. | 422/101 X |
| 4,279,863 | 7/1981 | Friehler | 422/101 X |

OTHER PUBLICATIONS

Publ. "A Simple Apparatus for Retrieving Density Gradients by Surface Tension", Glen S. Germain, Analytical Biochemistry, 1974, (pp. 89-92).

Primary Examiner—Daniel M. Yasich
Attorney, Agent, or Firm—William G. Gapcynski; Werten F. W. Bellamy; John M. Petruncio

[57] ABSTRACT

A float device is provided for density gradient fractionation which permits continuous removal of liquid samples from the surface of the liquid within a tube. The float device floats on the liquid surface and is provided with a centrally disposed length of tubing which extends through the device to provide communication between the liquid surface and a suction source such as a peristaltic pump. A concavity in the bottom of the float assists in removing trapped air and minimizes turbulent flow, thereby assuring high resolution of obtained samples.

2 Claims, 7 Drawing Figures

FLOAT DEVICE FOR DENSITY GRADIENT FRACTIONATION

FIELD OF THE INVENTION

The present invention relates to methods and apparatus for highly resolved fractional removal and sequential collection of samples of liquid including, but not limited to, fractionation of density gradient.

BACKGROUND OF THE INVENTION

The technique of density gradient centrifugation is widely used to isolate cellular macromolecules and organelles. Various kinds of devices have been designed to facilitate collection of fractions from density gradients in centrifuge tubes. These devices are employed in methods that generally involve displacement of the density gradient up or down the centrifuge tube by either a puncturing or a nonpuncturing procedure.

The earliest and simplest puncturing method was to pierce the bottom of the centrifuge tube with a small-bore hollow needle and to collect the emerging drops. Such a method is described in Weigle, J., Meselson, M., and Pagien, K. (1959) J. Mol. Biol. 1, 379–386. Improvements on this basis method involve (i) controlling the flow rate of the effluent or the speed at which air, distilled water, or mineral oil enter at the top, (ii) preventing the entry of air bubbles into the gradient, and (iii) reducing turbulent flow at the abrupt and narrow juncture between the tube bottom and the bore of the needle. These improvements are described in Szybalski, W. (1960) Experientia 16, 164; Heckly, R. J. (1960) Anal. Biochem. 1, 97–102; Englund, P. T., Smith, H. O., and Sandbeck, E. (1971) Anal. Biochem. 40, 490–493; Noll, H. (1969) Anal. Biochem. 27, 130–149; Tan, K. B. (1972) Anal. Biochem. 45, 306–308; Hopkins, T. R. (1973) Anal. Biochem. 53, 339–341; Clark, R. W., Carnes, J. D., and Arrighi, F. E. (1975) Anal. Biochem. 67, 139–146. Another puncturing method makes use of a small-diameter cannula which is inserted through the side or bottom of a centrifuge tube. A dense solution is pumped into the cannula displacing the gradient upward, thus delivering fractions from the top. Reference is made to the following articles for a further description of this technique: Hopkins, T. R. (1973) Anal. Biochem. 53, 339–341; Clark, R. W., Carnes, J. D., and Arrighi, F. E. (1975) Anal. Biochem. 67, 139–146; Brakke, M. K. (1963) Anal. Biochem. 5, 271–283; Bubel, H. C., and Riley, B. P. (1968) Anal. Biochem. 22, 335–337; Bresch, H., and Meyer, H. (1973) Anal. Biochem. 53, 199–207; and Romani, R. J., and Fisher, L. K. (1967) Anal. Biochem. 21, 333–335.

Nonpuncturing procedures usually employ a long narrow capillary tube that is carefully lowered down through the middle of a gradient to the bottom of the centrifuge tube. The capillary tube serves as an inlet to pump in air or to introduce a dense solution, thereby forcing the gradient upward and directing the fractions through a top outflow orifice. (See Oumi, T., and Osawa, S. (1966) Anal. Biochem. 15, 539–541; Liedtke, R., and Mosebach, K. O. (1974) Anal. Biochem. 62, 377–385 as well as the Hopkins article referred to above.) Suction may also be applied to the capillary tube to withdraw the gradient from the bottom of the centrifuge tube. This technique is described further in Fox, T. O., and Pardee, A. B. (1970) Science 167, 80–82. Another procedure uniquely eliminates the need to insert a capillary tube by utilizing a narrow recovery/-delivery channel that has been drilled the length of, and thus is already incorporated into, the thick wall of a specially fabricated centrifuge tube. Reference is made to Leif, R. C. (1968) Anal. Biochem. 25, 271–282. Fractionation by piston displacement involves forcing a specially tipped piston into a centrifuge tube from above and, with the use of continuously applied pressure, the tube contents are gradually displaced through the tip. Fractions are conveyed by collection tubing that is threaded through a channel in the piston shaft. (See Coombs, D. H. (1975) Anal. Biochem. 68, 95–101.) Another collecting apparatus consists of a plastic disk which is suspended through a hole in its center onto the flared end of a stretch of coiled tubing. The plastic disk is carefully pressed to the surface of the gradient until it becomes attached by surface tension. Suction is applied to the free end of the coiled tubing and, as the fractions are collected, the coiled tubing stretches while the descending fluid surface pulls the plastic disk with it. This technique is described in Germain, G. S. (1974) Anal. Biochem. 57, 89–92.

Although they are proposed and designed to improve the efficiency and ease of sample removal from density gradients, these methods and devices suffer from certain disadvantages. By retrieving gradients with puncturing techniques, mixing of contents can occur at the bottom of the tube owing to nonideal turbulent flow and contamination of successive fractions can arise when densely banded materials are collected through the slightly protruding narrow-bore needle. Movement of the entire gradient contents by displacement, either by puncturing or by nonpuncturing techniques, can introduce artifacts by wiping off material which has adhered to the tube wall and by dislodging material which has sedimented to the tube bottom. Expense becomes a consideration as tubes are destroyed by puncturing and as specialized accessory equipment is employed to ensure high performance and circumvent some of the previously mentioned problems. Many of the collecting devices are themselves highly complex and difficult to fabricate. Although inexpensive and simple to construct, the very design of the upper surface-following device described in the Germain article referred to above is a serious shortcoming. Severe mixing can occur because the surface fluid, before being drawn up into the bore of the collection tubing, is required to traverse radially across the flat disk to the central collecting point and move downward beneath the slightly protruding flared end of the tubing.

Patent references of possible interest include U.S. Pat. Nos. 275,134 (Burton); 536,858 (Donato); 1,591,923 (Lebherz); 3,955,423 (Ohringer); 3,960,727 (Hochstrasser); 3,972,683 (Lake); and 4,197,735 (Munzer et al), although, in general, these references are not concerned with fractionation of liquids.

SUMMARY OF THE INVENTION

In accordance with the invention, an apparatus and method are provided for highly resolved, sequential and continuous removal of samples from a liquid within a tube through the use of a plug-like member which floats on the surface of the liquid within the tube. A length of tubing extends centrally through the plug member to the liquid surface and enables the liquid to be drawn off from the top by a conventional peristaltic pump and collected by a conventional fraction collector. The plug is provided with a concavity in the bottom surface thereof which (i) facilitates removal of air trapped between the plug and the liquid surface at the beginning of the fractionation process and also (ii) assures high resolution of obtained samples by providing a gradually restricted cross section through which the liquid is drawn, thereby minimizing turbulent flow and the consequent mixing of iquid contents.

Although the invention is applicable for use in any clinical or research procedure requiring fractional removal of samples from liquid contained in tubes or the like, the invention has found specific use in fractionating of density gradients in centrifuge tubes to replace, or supplement, the techniques described above. The apparatus and method of the invention provide many advantages over such prior art techniques including cost, ease of construction and simplicity of use. The invention enables controlled, rapid, accurate fractionation and reproducible of liquids and can be used with tubes of any type material (glass, cellulose nitrate, polyallomer, etc.). The plug of the invention should form a relatively close fit with the tube in which is contained and the invention is readily adapted to tubes of different sizes by simply constructing the plug member of suitable dimensions. The invention also eliminates problems encountered in bottom fractionation described above, and, for example, provides a reduction of expenses because destruction of the associated tube is not required. In addition, the invention permits removal of successive samples from the upper surface of a liquid contained within a tube without disturbing the buk of the liquid. Further, the plug member is highly stable and steady with respect to placement thereof on the surface of the liquid and the apparatus can be readily connected to a flow cuvette and integrated into conventional fraction-collecting equipment. Finally, as noted above, the concavity or recess within the plug member facilitates removal of trapped air when fractionation begins and minimizes resolution by minimizing turbulent flow.

Other features and advantages of the invention will be set forth in, or apparent from, the detailed description of the preferred embodiments which follows.

DESCRIPTION OF A PREFERRED EMBODIMENT

Figure 1:
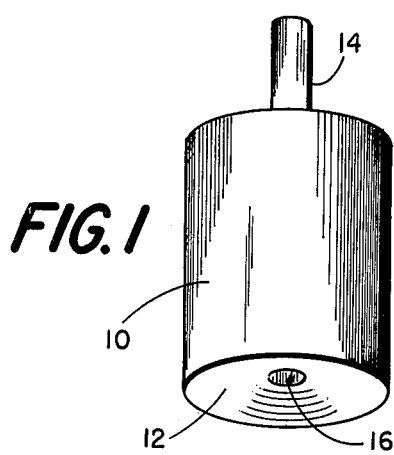
FIG. 1 is a perspective view of a plug or float device constructed in accordance with the present invention for use in density gradient fractionation.
Figure 2:
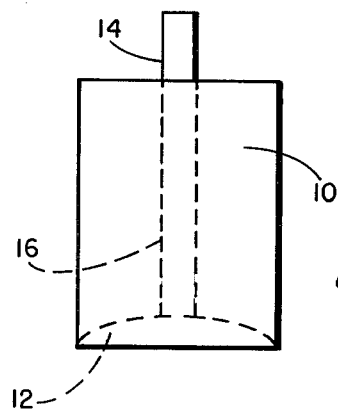
FIG. 2 is a side elevational view of the plug device of FIG. 1.

Referring to FIGS. 1 and 2, the plug-like float device of the invention is shown schematically in these figures and comprises a plug portion or plug 10 having a dome-shaped concavity or recess 12 formed in the lower face thereof and a drainage tube 14 located in plug 10 in a hole 16 drilled centrally in plug 10. The plug device, in an exemplary embodiment, is 11.8 mm. wide and 12.7 mm. long and readily machined from a standard 0.5-in.-diameter nylon rod (Read Plastics, Inc., Rockville, Md.). In this exemplary embodiment, a concavity 12 with a radius of 12.7 mm is routed into the lower face. The concavity at the plug bottom facilitates the removal of trapped air at the start of fractionation and also minimizes turbulent flow by gradually constricting the crosssectional area through which the sample flows. The tubing 14 in this embodiment is a length (38 mm) of 18-gauge stainlesssteel tubing firmly set into hole 16 drilled lengthwise through the center of the plug 10. The dimensions referred to above are designed to accommodate a tube of 0.5 in. (12.7 mm) inside diameter; however, it will be appreciated that the design is readily adapted to other tube sizes by simply altering the dimensions of the nylon plug.

Figure 3:
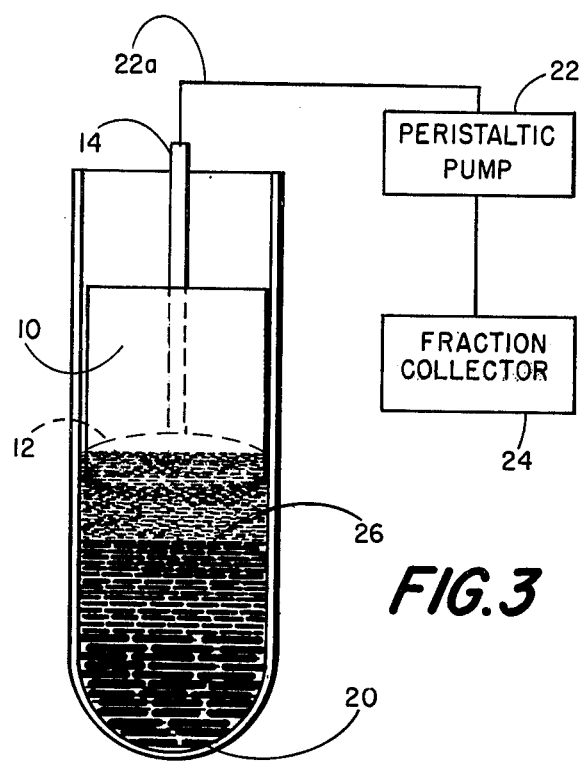
FIG. 3 is a schematic cross sectional view of the plug device of FIGS. 1 and 2 showing the device in use.

Referring to FIG. 3, the plug or float device 10 is shown in use with a density gradient fractionation system including a centrifuge tube 20, a peristaltic pump 22 and a fraction collector 24. Peristaltic pumps and fraction collectors are, of course, commercially available devices and any of these devices should be suitable for the purpose of the invention. The centrifuge tube is placed in a holder (not shown) and the device 10 is floated on the surface of the density gradient indicated schematically at 26. To improve resolution, the length and volume of the conducting tubing are kept to a minimum. In a specific example, lightweight polyethylene tubing (i.d. of 0.023 and o.d. of 0.038 in.) was attached to the stainless-steel tubing 14 of the device 10 and connected to Tygon tubing 22a (i.d. of 0.032 and o.d. of 0.095 in.) of the peristaltic pump 22. To further improve resolution, the peristaltic pump 22 was operated at a sufficiently low setting for continuous, not pulsatile, flow. Since a portion of the gradient contents filled in the small space (0.1 mm) between the device and the wall of the centrifuge tube 20, 0.15 ml of distilled water was gently layered on the gradient prior to the careful lowering of the nylon plug 10 onto the surface of the gradient 26. The peristaltic pump 22 was then used to start the collection of fractions.

In order to test the performance of the device 10, measurements were made with respect to the ability of the device to resolve closely spaced bands of progressively decreasing concentrations of blue dextran 2000 sandwiched between the layers of a discontinuous sucrose gradient. Discontinuous, so-called "sandwich", gradients were prepared by filling a centrifuge tube with 0.5-ml layers of sucrose solutions beginning with 20% sucrose and decreasing stepwise by 2% to a final concentration of 4%. Alternate layers contained blue dextran 2000 (Pharmacia), a high molecular weight absorbancy marker, beginning with 0.3% and increasing linearly by 0.1% to a final concentration of 0.6%. To minimize diffusion of the marker, the sucrose solutions were rapidly, but carefully, layered and the gradients were fractionated immediately. Fractions (0.1 ml) were diluted to 1 ml with distilled water and the absorbancy was determined at 625 nm.

Figure 4A:
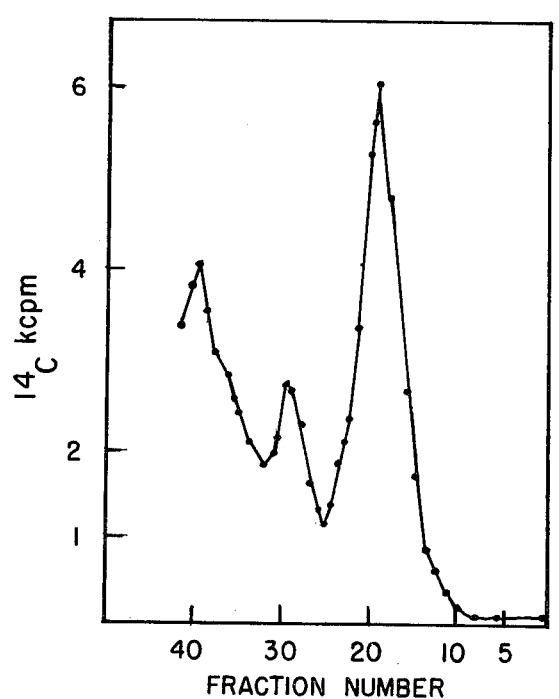
FIGS. 4(a), 4(b), 4(c) and 4(d) are curves used in comparing the results produced by the plug device of the invention with prior art puncturing techniques.
Figure 4C:
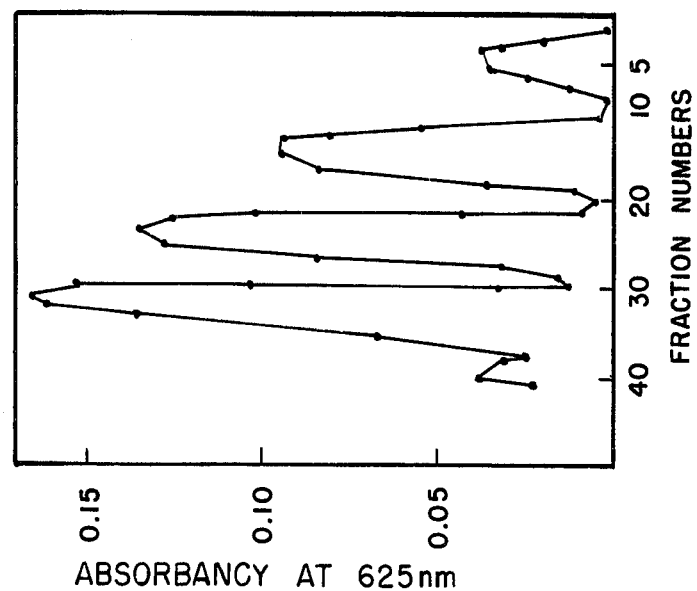
Figure 4B:
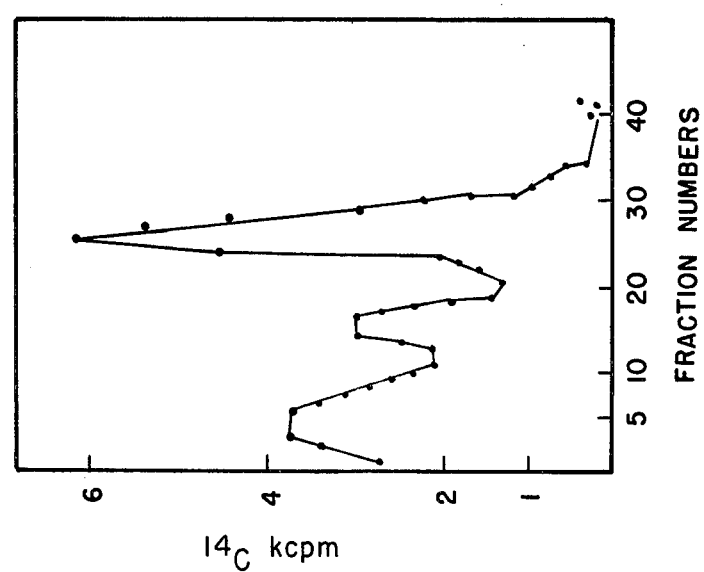
Figure 4D:
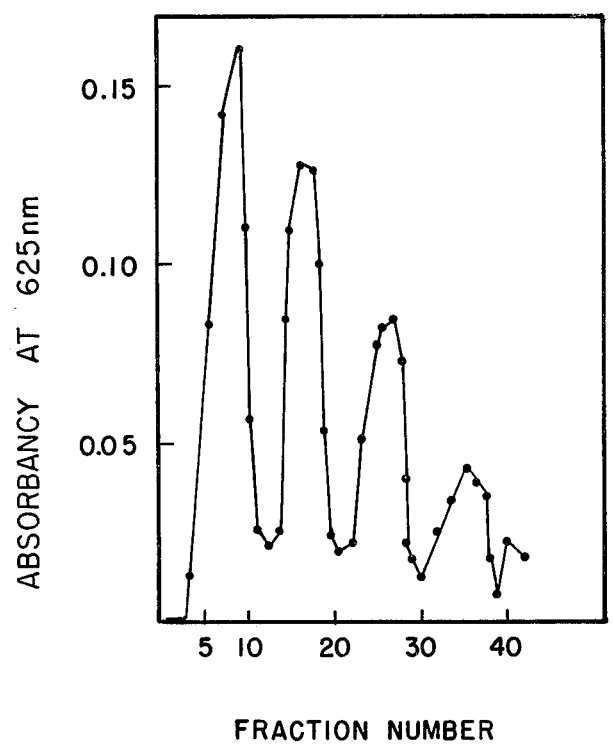

Duplicate "sandwich" gradients were prepared: one was top fractionated by the nylon plug device of the invention, and the other by a bottom-puncturing setup manufactured by Buchler Instruments. The results for the top fractionating technique and the bottom-puncturing setup are illustrated in FIGS. 4(c) and 4(d) respectively. To facilitate comparison, the absorbancy pattern of FIG. 4(c) was reversed to conform to that of FIG. 4(d). Excellent resolution was obtained by top or bottom collecting and the fractionated gradients products almost identical patterns displaying four, sharply symmetrical and linearly decreasing peaks of absorption.

The resolving power of the device of the invention was further tested in a typical analytical application. A crude bacterial extract was prepared to contain ribosomal subunits and was analyzed by sedimentation in a linear sucrose density gradient. Cultures of *Bacillus megaterium* were grown in trypticase soy broth (BBL) in the presence of [$^{14}$C] uracil, wherein the symbol [$^{14}$C] represents carbon 14. Cells were harvested during the early exponential phase of growth, washed three times with, and finally suspended in, a buffer-salt solution (pH 7.5) of 10 mM Tris-Cl, 0.1 mM Mg-acetate, 150 mM NH$_4$Cl, and 6 nM 2-mercaptoethanol. A crude extract was prepared by passage through a French pressure cell. Duplicate 0.15-ml samples of the extract were layered on 5 to 20% linear sucrose gradients (4.4 ml each) prepared in the same buffer-salt solution. The gradients were centrifuged in a Beckman SW 50.1 rotor at 45,000 rpm for 105 min at 5° C. Tube contents were collected in two-drop fractions (approximately 0.1 ml). Radioactivity was determined by rinsing the fractions directly into vials containing "Instabray" scintillation fluid (Yorktown Research) and counting in a scintillation spectrometer (Nuclear-Chicago, 720 series).

FIGS. 4(*a*) and 4(*b*) show the sedimentation profiles of the crude extract, with FIG. 4(*a*) corresponding to bottompuncturing and FIG. 4(*b*) to use of the plug device of the invention in top fractionating. As in the preceding experiment, the profile of FIG. 4(*a*) (fractionation by bottom puncturing), was reversed to conform to that of FIG. 4(*b*) (top collecting). Again, almost identical profiles were obtained with the larger 50 S ribosomal peak clearly resolved from the smaller 30 S peak. A peak of lighter RNA material can be seen at the top of the gradients.

As will be appreciated from the foregoing, the simple top collecting plug device of the invention makes it possible to fractionate gradients in a highly resolved, continuous, easy, inexpensive, accurate, and reproducible manner, while precluding contamination by excessively sedimented material. The plug-like device of the invention has been demonstrated to at least be equal to conventional systems in resolving ability and, in addition, offers numerous other advantages. In particular, as stated above, the device of the invention (i) is simple to use and easy to construct, (ii) permits controlled, rapid, highly resolved accurate and reproducible fractionation of density gradients, (iii) can be readily connected to a flow cuvette and integrated into automatic analyzing or fractioncollecting equipment, (iv) reduces expenses by not requiring the destruction of tubes, (v) does not necessitate the use of only cellulose nitrate tubes, and (vi) offers, when used in combination with tube-puncturing equipment, the versatility of collecting fractions from either the top or bottom of density gradients.

Although the invention has been described in relation to an exemplary embodiment thereof, it will be understood by those skilled in the art that variations and modifications can be effected in this exemplary embodiment without departing from the scope and spirit of the invention.

We claim:

1. In a system for fractional removal and collection of samples of a liquid contained in a tube comprising pump means for pumping out said samples of the liquid from said tube and collector means for separately collecting said samples, the improvement comprising a cylindrical plug device which floats on the surface of the liquid in the tube and which includes a length of sample conveyance tubing extending centrally therethrough in communication with the upper surface of the liquid in the tube, said plug device includes a concavity in the bottom surface thereof which facilitates the removal of air trapped between the bottom of said plug and the surface of the liquid prior to fractionation of said liquid and assures high resolution of sequential samples by minimizing turbulent flow and the consequent mixing of said liquid, and tube means for connecting said sample conveyance tubing to said pump means of the system so as to permit sequential and highly resolved removal of said samples in said tube from the upper surface of said liquid.

2. A system as claimed in claim 1 wherein said plug is fabricated of nylon and said conveyance tubing comprises a length of metal tubing fitted into a central bore drilled through said plug, the outside diameter of said plug being slightly less than the inside diameter of the tube.

* * * * *